US008383048B2

(12) United States Patent
van Hal et al.

(10) Patent No.: US 8,383,048 B2
(45) Date of Patent: Feb. 26, 2013

(54) MICROSENSOR FOR MERCURY

(75) Inventors: Ronald E. G. van Hal, Watertown, MA (US); Hua Chen, Cambridge, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 20 days.

(21) Appl. No.: 12/840,492

(22) Filed: Jul. 21, 2010

(65) Prior Publication Data
US 2012/0021524 A1    Jan. 26, 2012

(51) Int. Cl.
*G01N 30/96*    (2006.01)

(52) U.S. Cl. .................... 422/88; 422/82.01; 422/82.04; 422/82.02; 422/90; 422/94; 422/98

(58) Field of Classification Search .................. 422/401, 422/402, 82.02, 82.04, 88, 90, 94, 98, 82.01
See application file for complete search history.

(56) References Cited

U.S. PATENT DOCUMENTS

| | | | |
|---|---|---|---|
| 3,950,980 A | 4/1976 | Braun et al. | |
| 4,651,564 A | 3/1987 | Johnson et al. | |
| 4,822,465 A | 4/1989 | Jones et al. | |
| 4,928,513 A * | 5/1990 | Sugihara et al. | 73/25.03 |
| 5,367,283 A | 11/1994 | Lauf et al. | |
| 5,759,493 A | 6/1998 | Raisanen | |
| 5,891,395 A * | 4/1999 | Glaunsinger et al. | 422/53 |
| 5,985,673 A * | 11/1999 | Bao et al. | 436/151 |
| 5,992,215 A | 11/1999 | Caron et al. | |
| 7,228,725 B2 | 6/2007 | Salter et al. | |
| 7,441,440 B2 | 10/2008 | Sberveglieri et al. | |
| 2004/0099047 A1 * | 5/2004 | Raisanen | 73/25.05 |
| 2006/0257286 A1 | 11/2006 | Adams | |
| 2008/0163694 A1 | 7/2008 | Haskell et al. | |

FOREIGN PATENT DOCUMENTS
WO    2009077183 A1    6/2009

OTHER PUBLICATIONS

Anonymous, "Jerome Hydrogen Sulfide Analyzers," Arizona Instrument LLC, Energy Institute Meeting, Oct. 2005: pp. 1-17.
International Search Report of PCT Application Serial No. PCT/US2011/037150 dated Feb. 9, 2012.
Clevenger et al., "Trace Determination of Mercury: A Review," Critical Reviews in Analytical Chemistry, 1997, vol. 27(1): pp. 1-26.

(Continued)

*Primary Examiner* — Krishnan S Menon
*Assistant Examiner* — Dwan A Gerido
(74) *Attorney, Agent, or Firm* — Jakub M. Michna; Rachel Greene; Brigid Laffey

(57) ABSTRACT

Methods and devices for detecting a concentration of one or more element in hydrocarbon and/or natural gas in a oil and gas field application. The device including a microstructure having a low thermal mass suspended within a channel, the microstructure includes a supporting layer and a insulating layer; a controllable thermal device in communication with the supporting layer of the microstructure, wherein the controllable thermal device is controllably heated to one or more release temperature of the one or more element; a sensing layer arranged on the insulating layer to absorb molecules of the one or more element from hydrocarbon and/or natural gas; a detecting and measuring resistance device in communication with the sensing layer for measuring the resistance changes caused by absorption of molecules of the one or more element onto the sensing layer at a first temperature and a second temperature, and storing the data on a processor.

18 Claims, 9 Drawing Sheets

OTHER PUBLICATIONS

Drelich et al., "Laboratory Tests on Mercury Emission Monitoring with Resonating Gold-coated Silicon Cantilevers," Environ. Sci. Technol., 2008, vol. 42(6): pp. 2072-2078.

McNerney et al., "Mercury Detection by Means of Thin Gold Films," Science, vol. 178, 1972: pp. 611-612.

Mirsky et al., "Chapter 12: Chemical sensors for mercury vapour," Comprehensive Analytical Chemistry, 2007, vol. 49: pp. 235-251.

Schambach et al., "Micromachined Mercury Sensor," ESSDERC, 2002: p. 443-446.

* cited by examiner

MICROSENSOR FOR MERCURY

BACKGROUND

This patent specification relates generally to oil and gas field applications. More particularly, this patent specification relates to devices and methods for detecting mercury in hydrocarbon fluids and/or natural gas during oil and gas field applications.

The are many approaches for the development of sensors for detecting concentrations of selected components in gaseous mixtures, for example determining mercury and hydrogen sulfide concentrations are cold vapour atomic fluorescence spectroscopy (CV-AFS) and cold vapour atomic absorption spectroscopy (CV-AAS), which, although extremely sensitive, have certain serious limitations. These methods are used in laboratories and could hardly be used at the well site or even in a downhole application. There are other methods to determine the mercury and hydrogen sulfide concentrations like X-ray fluorescence, neutron activity analysis, atomic emission spectroscopy and mass spectroscopy. However, they all are suitable for laboratory applications and lack suitability for oilfield applications such as well site and/or downhole applications.

Typically, mercury is trapped on gold, silver or an activated charcoal for determining concentration and sampling purposes. In the oil and gas industry, the sampling uses of gold amalgamation and further analysis are done in a remote laboratory away from the well site and/or downhole.

Some of the known approaches for the development of a mercury sensor include the use of thin film gas sensors developed to detect a selected component in a composite gas. For example, a thin film gas sensor is formed of a suitable semiconductor material whose electrical resistivity changes in response to the adsorption of the selected component. The thin film gas sensor can include a gold thin metal film layer deposited on a substrate, wherein the resistivity of the gold changes in response to the adsorption of mercury. The electrical resistance of the gold film exposed to the gas is then measured and can provide a basis for determining the concentration of the selected component.

The adsorption of mercury to gold as a surface process can result in the diffusion of the gold being much slower than the adsorption on the surface and uptake from the surface. As long as the amount of mercury adsorbed is lower than the maximum surface concentration value, the adsorption occurs with a sticking probability close to unity. The slower diffusion leads to saturation of the gold surface with mercury and block further adsorption. This effect can occur when about 50% of the gold surface is saturated with mercury. An increasing temperature decreases the amount of absorbed mercury.

Further, an increased mercury exposure time up to hours and/or very high mercury concentrations leads to the formation of mercury aggregates in the form of islands or three-dimensional dendritic structures on/in the gold layer. This is considered one of the main limitations in the implementation of thin film gold sensors for mercury monitoring.

Another disadvantage of gold layer mercury sensors is their poor selectivity. The sensor has a cross-sensitivity towards water vapour, sulphuric acid vapour, sulfides, thiols and iodine. It was shown that the use of self-assembled monolayers of hexadecanethiol can decrease the sensitivity to these components dramatically except for iodine. Mercury has been shown to be able to penetrate the monolayer and give a response that is close to 50% of a bare electrode.

A number of transducers have been used for the detection of mercury based on its absorbance to gold. Most of them use a gold layer with a particular thickness. Transducers that measure the increase in mass can include quartz microbalance, surface acoustic wave and micro-cantilevers. The transducer principles that use optical techniques can include surface Plasmon resonance whereas localized plasmon resonance is suggested but not implemented for mercury sensors. Finally, the adsorption of mercury by gold leads to an increase in surface electrical resistance. Conductometric transducers can measure particular levels of mercury concentrations. The sensitivity of this type of measurement decreases with an increase of the thickness of the gold layer. Desorption of the adsorbed mercury can be achieved by heating the sensor to very high temperatures; however, it comes with at a cost.

For example, adsorptive thin film gas sensors can be regenerated after adsorbing a sufficient amount of the selected component to trigger an indication circuit. The regeneration of the thin film involves heating the thin film to a very high temperature to liberate the molecules of the selected component adsorbed by the thin film layer, i.e., the gold film, to prepare the gas sensor for a new cycle of gas detection and measurement. Depending upon the type of molecules adsorbed, the regeneration temperature can be a very high temperature. In prior art devices, the thin film layer is commonly used in both the sensing role and as a heater conductor for regeneration.

However, thin film layers that are commonly used as both the sensing role and as a heater conductor for regeneration which results in a limited operational life. One of the main reasons for the failure of the mechanism can involve the electromigration of the gold metal in the sensing film. Electromigration is the transport of material caused by the gradual movement of the ions in a conductor due to the momentum transfer between conducting electrons and diffusing metal atoms. The effect is important in applications where high direct current densities are used, such as in microelectronics and related structures. As the structure size in electronics such as integrated circuits (ICs) decreases, the practical significance of this effect increases. Thus, the result of electromigration is that metal atoms move from the thin gold film into the dividing layers on a chip. If electromigration occurs to a great degree, and enough metal atoms move into the dividing layers, the thin gold film may become too thin, resulting in failure of the gas sensor. So, electromigration can be furthered when the thin film layer is used as a sensor and as a heater conductor. The sensor and heater thin film gas sensor likely fails after a small number of cycles of sensing and regeneration due to the high re-evaporation temperature.

Along with the problem of electromigration, the sensor and heater thin film gas sensors have a lower sensitivity that is needed. The sensitivity of a combined sensor and heater thin film gas sensor can be dictated by its design. Another problem with the sensor and heater thin film gas sensors is that the resistance of their trace can be high. Therefore, a high voltage (approximately 60-100 volts) is needed to regenerate the sensor. Consequently, the sensor and heater thin film gas sensors are often limited in use to areas where 120 VAC or suitable power generators are available.

Some prior art thin film gas sensors circumvent the above-noted problems found with the sensor and heater thin film gas sensors by utilizing external heating elements to heat the thin metal film to the regeneration temperature. Unfortunately, such external heating elements can be difficult to manufacture and to calibrate for specific sensor applications. Moreover, the amount of heat generated by such a heating element may vary over the surface of the sensing layer. Uneven heating is undesirable because it can cause insufficient or inconsistent regeneration.

Therefore, there is a need for methods and systems for detecting mercury and hydrogen sulfide in hydrocarbon fluids and natural gas during oil and gas field applications.

SUMMARY

According to some embodiments, an oil and gas field application device for detecting a concentration of one or more element in one of hydrocarbon or natural gas in a wellsite, subterranean environment or both. The oil and gas field application device comprising: a microstructure having a low thermal mass suspended within a channel, the microstructure includes a supporting layer and a insulating layer; at least one controllable thermal device in communication with the supporting layer of the microstructure, wherein the at least one controllable thermal device is controllably heated to one or more release temperature of the one or more element; a sensing layer arranged on the insulating layer to absorb molecules of the one or more element from one of hydrocarbon or natural gas; and a detecting and measuring resistance device in communication with the sensing layer for measuring the resistance changes caused by absorption of molecules of the one or more element onto the sensing layer at a first temperature and a second temperature, and storing the data on a processor.

According to an aspect of the oil and gas field application device, the one or more element includes mercury (Hg) or hydrogen sulfide ($H_2S$). Further, the microstructure can be made of an electrical insulating and thermal conducting material and the oil and gas field application includes one of a wellsite, subterranean environment or downhole environment. Further still, the electrical insulating and thermal conducting material can be from the group consisting of one of titanium nitride (TiN), silicon nitride ($Si_3N_4$), aluminum nitride (AlN), silicon oxide ($SiO_2$), silicon or some combination thereof. It is possible the at least one controllable thermal device is a conductive pathway disposed over and substantially covers a surface area of the supporting layer of the microstructure and controls the temperature of the microstructure up to approximately 400 C. The at least one controllable thermal device can be activated to controllably heat the microstructure and the sensing layer to a regeneration temperature sufficient to cause the molecules of the one or more element to be liberated from the sensing layer.

According to an aspect of the oil and gas field application device, it may further comprise of a layer applied on the supporting layer for facilitating adhesion of the controllable thermal device to the microstructure. It is possible it may comprise of a layer deposited on the insulating layer for facilitating adhesion of a sensing layer to the microstructure.

According to an aspect of the oil and gas field application device, an electrical resistivity of the sensing layer changes when the molecules of the one or more element can be absorbed by the sensing layer, and the at least one controllable thermal device may be activated when the electrical resistivity reaches a predetermined resistivity threshold. Further, it may further comprise of a metal pathway deposited on the insulating layer to the microstructure, the metal pathway having an affinity for the one or more element. It is noted that the metal pathway can be from the group consisting of gold, black gold, silver, copper, palladium chloride, an alloy material or some combination thereof.

According to an aspect of the oil and gas field application device, it may further comprise of a reference sensing layer positioned on a portion of the insulating layer. Further, it is possible it may further comprise of: 1) an electrical resistivity of the reference sensing layer changes when the molecules of the one or more element are absorbed by the reference sensing layer, and the at least one controllable thermal device is activated when the electrical resistivity reaches a predetermined resistivity threshold; 2) a conductive pathway deposited on the insulating layer of the microstructure including the portion of the insulating layer, the metal pathway having a affinity for the one or more element such that the reference sensing layer and sensing layer are in communication with the conductive pathway; and 3) a gas impermeable layer is applied on the portion of the insulating layer of the conductive pathway so as to result in the reference sensing layer to have no absorption.

According to an aspect of the oil and gas field application device, the microstructure can be one of non-linear such as wave-like so as to provide a disturbance in a flow of a fluid through the channel. Further, the microstructure is structured and arranged to have a variable thickness to provide a disturbance in a flow of a fluid flowing through the channel.

According to an embodiment, the oil and gas field application device can be detecting two or more elements in one of hydrocarbon or natural gas. The oil and gas field application device comprises of a multi-zone microstructure having a low thermal mass suspended within a channel. Wherein the multi-zone microstructure includes: a first zone with a first supporting layer and a first insulating layer; a second zone having a second supporting layer and a second insulating layer; and at least two controllable thermal devices, a first controllable thermal device in communication with the first supporting layer and a second controllable thermal device in communication with the second supporting layer and is capable of controlling the temperature up to approximately 400 C. Further, the first controllable thermal device of the first zone controllably varies the temperature within a first range of temperatures. The second controllable thermal device of the second zone controllably varies the temperature for a second range of temperatures, such that the range of temperature for one of the first controllable thermal device, the second controllable thermal device or both is controllable up to a release temperature of the two or more elements. Further still, a first sensing layer can be arranged on the first insulating layer, wherein the first sensing layer is arranged to absorb molecules of the two or more elements from the one of hydrocarbon or natural gas at a first sensitivity for a first element and a second sensitivity for a second element. The second sensing layer can be arranged on the second insulating layer, wherein the second sensing layer arranged to absorb molecules of the two or more elements from the one of hydrocarbon or natural gas at a third sensitivity for the first element and a fourth sensitivity for the second element. Finally, at least one processor can be in communication with the at least two controllable thermal devices and the first and second sensing layers.

According to an aspect of the oil and gas field application device, one of the first insulating layer, the second insulating layer or both include a reference sensing layer positioned on a portion of the insulating layer. Further, the oil and gas field application device may further comprise of: 1) an electrical resistivity of the reference sensing layer changes when the molecules of the one or more element are absorbed by the reference sensing layer, and the at least one controllable thermal device is activated when the electrical resistivity reaches a predetermined resistivity threshold; 2) a conductive pathway deposited on the insulating layer, the metal pathway having a affinity for the one or more element such that the reference sensing layer and at least one sensing layer of the two or more sensing layers are in communication with the conductive pathway; and 3) a gas impermeable layer is applied on the insulating layer of the conductive pathway so as to result in the reference sensing layer to having no absorption.

According to an aspect of the oil and gas field application device, the two or more elements may include mercury and hydrogen sulfide ($H_2S$) and the oil and gas field application includes one of a wellsite, subterranean environment or downhole environment. Further, the multi-zone microstructure can be one of non-linear such as wave-like so as to provide a disturbance in a flow of a fluid through the channel. Further still, the multi-zone microstructure can be structured and arranged to have a variable thickness to provide a disturbance in a flow of a fluid flowing through the channel. It is possible the microstructure can be made of an electrical insulating and a thermal conducting material. Further, the electrical insulating and thermal conducting material can be from the group consisting of one of titanium nitride (TiN), silicon nitride ($Si_3N_4$), aluminum nitride (AlN), silicon oxide ($SiO_2$), silicon or any combination thereof. Further still, the first sensing layer can be made of a different material than the second sensing layer.

According to an aspect of the oil and gas field application device may further comprise of: 1) a detection and measuring resistance device in communication with the first sensing layer for measuring the resistance changes caused by absorption of molecules of the first element onto the first sensing layer at a first temperature and a second temperature within the first range; and 2) wherein the detection and measuring resistance device is also in communication with the second sensing layer for measuring the resistance changes caused by absorption of molecules of the second element onto the second sensing layer at a first temperature and a second temperature within the second range.

According to at least one embodiment, a device for detecting two or more elements in hydrocarbon and/or natural gas in a wellsite, a subterranean environment or both. The device comprising: a multi-zone microstructure having a low thermal mass suspended within a channel, the multi-zone microstructure including: 1) a first zone with a first supporting layer and a first insulating layer; 2) a second zone having a second supporting layer and a second insulating layer; and 3) at least two controllable thermal devices, a first controllable thermal device in communication with the first supporting layer and a second controllable thermal device in communication with the second supporting layer, such that the at least two controllable thermal devices are capable of controlling the temperature up to approximately 400 C. Wherein, the first controllable thermal device of the first zone controllably varies the temperature within a first range of temperatures. The second controllable thermal device of the second zone controllably varies the temperature for a second range of temperatures, such that the range of temperature for one of the first controllable thermal device, the second controllable thermal device or both is controllable up to a release temperature of the two or more elements. Further including: 1) a first sensing layer arranged on the first insulating layer, the first sensing layer arranged to absorb molecules of the two or more elements from the one of hydrocarbon or natural gas at a first sensitivity for a first element and a second sensitivity for a second element; 2) a second sensing layer arranged on the second insulating layer, the second sensing layer arranged to absorb molecules of a second element of the two or more elements from the one of hydrocarbon or natural gas at a third sensitivity for the first element and a fourth sensitivity for the second element; 3) a detection and measuring resistance device in communication with the first sensing layer for measuring the resistance changes caused by absorption of molecules of the first element onto the first sensing layer at a first temperature and a second temperature within the first range. Wherein the detection and measuring resistance device is also in communication with the second sensing layer for measuring the resistance changes caused by absorption of molecules of the second element onto the second sensing layer at a first temperature and a second temperature within the second range; and finally 4) at least one processor in communication with the at least two controllable thermal devices, the first and second sensing layers and the detection and measuring resistance device.

According to at least one embodiment, an apparatus for use in a oil and gas field application for detecting one of mercury (Hg) or hydrogen sulfide ($H_2S$) in one of hydrocarbon or natural gas in a wellsite, subterranean environment or both. The apparatus comprising: 1) a microstructure having a low thermal mass suspended within a channel that is structured and arranged for an oil and gas field application environment, the microstructure includes a supporting layer and a insulating layer; 2) at least one controllable thermal device in communication with the supporting layer of the microstructure, wherein the at least one controllable thermal device controls the temperature up to a release temperature of one of the mercury (Hg) or the hydrogen sulfide ($H_2S$) and is capable of controlling the temperature up to approximately 400 C; 3) a sensing layer arranged on the insulating layer to absorb molecules of one of the mercury (Hg) or hydrogen sulfide ($H_2S$) from one of hydrocarbon or natural gas; 4) a detecting and measuring resistance device in communication with the sensing layer for measuring the electrical resistance changes caused by absorption of molecules of one of the mercury (Hg) or hydrogen sulfide ($H_2S$) onto the sensing layer at a first temperature and a second temperature up to approximately 400 C; and finally 5) at least one processor in communication with the at least one controllable thermal device, the sensing layer and the detection and measuring resistance device, such that the at least one controllable thermal device is activated when the electrical resistivity reaches a predetermined resistivity threshold.

According to an embodiment, a method for detecting a concentration of one or more element from one of hydrocarbon or natural gas in an oil and gas field application, wherein the oil and gas field application includes a wellsite and a subterranean environment. The method comprising: a) exposing at least one sensing layer arranged on a portion of an insulating layer of a microstructure to one of hydrocarbon or natural gas for a first period of time; b) measuring resistance caused by absorption of molecules of a first element of the one or more element onto the at least one sensing layer with a detecting and measuring resistance device in communication with the at least one sensing layer and recording first element resistance data on a processor; c) controllably heating at least one controllable thermal device in communication with a portion of a supporting layer of the microstructure, wherein the at least one controllable thermal device controllably varies the temperature of the microstructure up to a release temperature of the first element and for a second period of time; d) measuring resistance of the first element on the sensing layer with the detecting and measuring resistance device and recording the released first element resistance data on the processor; e) controllably heating the at least one controllable thermal device up to a release temperature of the second element and for a third period of time; f) measuring resistance of the second element on the at least one sensing layer with the detecting and measuring resistance device and recording the released second element resistance data on the processor; and g) determining the concentration of one or more element.

According to an aspect of the method, step b) further comprises: 1) waiting for a second period of time so the at least one sensing layer cools; and 2) re-measuring resistance caused by absorption of molecules of the first element of the one or more element onto the at least one sensing layer with the detecting and measuring resistance device and recording cooled first element resistance data on the processor. Further, the first period of time is substantially longer in time than any other period of time including the second period of time, the third period of time, the fourth period time, etc. Further still, the second period of time is substantially less than the first period of time. It is possible; the third period of time is substantially less than the second period of time. Also, the first element is mercury (Hg) and the second element is hydrogen sulfide ($H_2S$).

According to an embodiment, an oil and gas field application device for detecting two or more elements in one of hydrocarbon or natural gas. The oil and gas field application device comprising: a multi-zone microstructure having a low thermal mass suspended within a channel, the multi-zone microstructure includes: 1) a first zone with a first supporting layer and a first insulating layer; 2) a second zone having a second supporting layer and a second insulating layer, such that the second zone is maintained at a temperature B; and 3) at least two controllable thermal devices, a first controllable thermal device in communication with the first supporting layer and a second controllable thermal device in communication with the second supporting layer and is capable of controlling the temperature up to approximately 400 C. Wherein the first controllable thermal device of the first zone maintains at a temperature A and the second controllable thermal device of the second zone maintains at a temperature B. The first controllable thermal device, the second controllable thermal device or both is controllable up to a release temperature of the two or more elements; wherein: 1) a first sensing layer arranged on the first insulating layer, the first sensing layer arranged to absorb molecules of the two or more elements from the one of hydrocarbon or natural gas at a first sensitivity for a first element and a second sensitivity for a second element; 2) a second sensing layer arranged on the second insulating layer, the second sensing layer arranged to absorb molecules of the two or more elements from the one of hydrocarbon or natural gas at a third sensitivity for the first element and a fourth sensitivity for the second element; and 3) at least one processor in communication with the at least two controllable thermal devices and the first and second sensing layers.

According to an aspect of the method, the temperature A is at a temperature up to a release temperature of the first element of the two or more elements, and wherein the temperature B is at a temperature above the release temperature of the first element and below the release temperature of the second element of the two or more elements.

Further features and advantages will become more readily apparent from the following detailed description when taken in conjunction with the accompanying drawings.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 9A shows a non-linear shape (e.g., wave-like) of the microstructure, and FIG. 9B shows a variable thickness microstructure, so as to provide a disturbance in a flow of a fluid flowing through the channel, according to some embodiments.

DETAILED DESCRIPTION OF THE PREFERRED EMBODIMENTS

Figure 1:
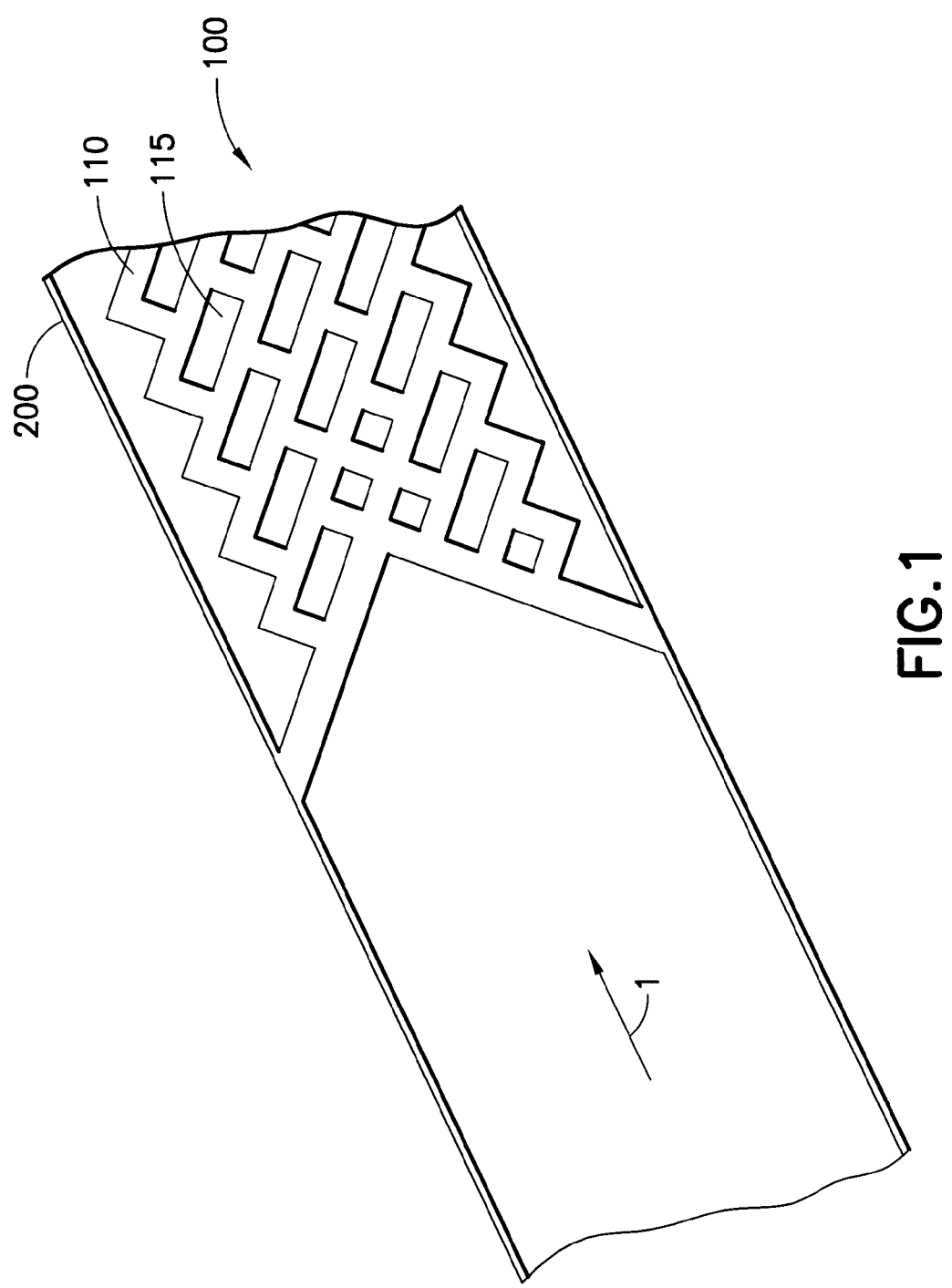
FIG. 1 illustrates a perspective view of a device with a low thermal mass suspended within a channel having varying shaped etching holes, according to some embodiments.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, well-known processes, structures, and techniques may be shown without unnecessary detail in order to avoid obscuring the embodiments. Further, like reference numbers and designations in the various drawings indicated like elements.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

According to some embodiments, for purposes of the following discussion, the "device", "sensor device" or "conductometric sensor" or "oil and gas field application device" is able to detect mercury and/or hydrogen sulfide. Of course, the present invention need not be limited to the detection of mercury and/or hydrogen sulfide. Rather, those skilled in the art will recognize that the microstructure may be adapted such that other gases or compounds may be monitored.

According to some embodiments, an oil and gas field application device for detecting a concentration of one or more element in one of hydrocarbon or natural gas in a wellsite, subterranean environment or both. The oil and gas field application device comprising: a microstructure having a low thermal mass suspended within a channel, the microstructure includes a supporting layer and a insulating layer; at least one controllable thermal device in communication with the supporting layer of the microstructure, wherein the at least one controllable thermal device is controllably heated to one or more release temperature of the one or more element; a sensing layer arranged on the insulating layer to absorb molecules of the one or more element from one of hydrocarbon or natural gas; and a detecting and measuring resistance device in communication with the sensing layer for measuring the resistance changes caused by absorption of molecules of the one or more element onto the sensing layer at a first temperature and a second temperature, and storing the data on a processor.

Referring to FIG. 1, FIG. 1 shows a perspective view of a device (or conductometric sensor) 100 within a channel 200, in accordance with a preferred embodiment of the present invention. FIG. 1 shows the device having etching holes 115 in a microstructure or substrate 110. The etching holes 115 may be shaped such as: a varied shape, a geometric shape, a non-uniform shape or a uniform shape. The device 100 is configured to detect the presence of a specified component (such as, mercury vapor or hydrogen sulfide vapor) within hydrocarbon fluids and/or natural gas. Hydrocarbon fluids and/or natural gas is represented by arrow 1, enters through an inlet (not shown), flows around device 100, and exits via an outlet (not shown). It is noted for application the "specified component" is mercury or hydrogen sulfide vapor. Of course, the present device need not be limited to the detection of mercury or hydrogen sulfide vapor or the analysis of hydrocarbon fluids and/or natural gas samples. Rather, those skilled in the art will recognize that device 100 may be adapted such that other gases or compounds may be monitored.

It is noted the device maybe referred to as a conductometric sensor, a conductometric mercury sensor, a thin film gas sensor, a oil and gas field application device or a sensor device. The device maybe fabricated with microtechnology. In microtechnology, it is possible to fabricate thin suspended structures in a channel. It is noted that the term channel may also include, a channel like structure, a tube, a pipe, a flowline, or a similar like structure. In microtechnology, it is possible to fabricate thin suspended structures that include etching holes. The etching holes maybe of a uniform shape, non-uniform shape or some combination thereof. It is possible the etching holes maybe symmetrical, non-symmetrical, uniformly arranged, non-uniformly arranged or some combination thereof. The device maybe shaped uniformly, non-uniformly or geometrically within the channel.

Figure 2:
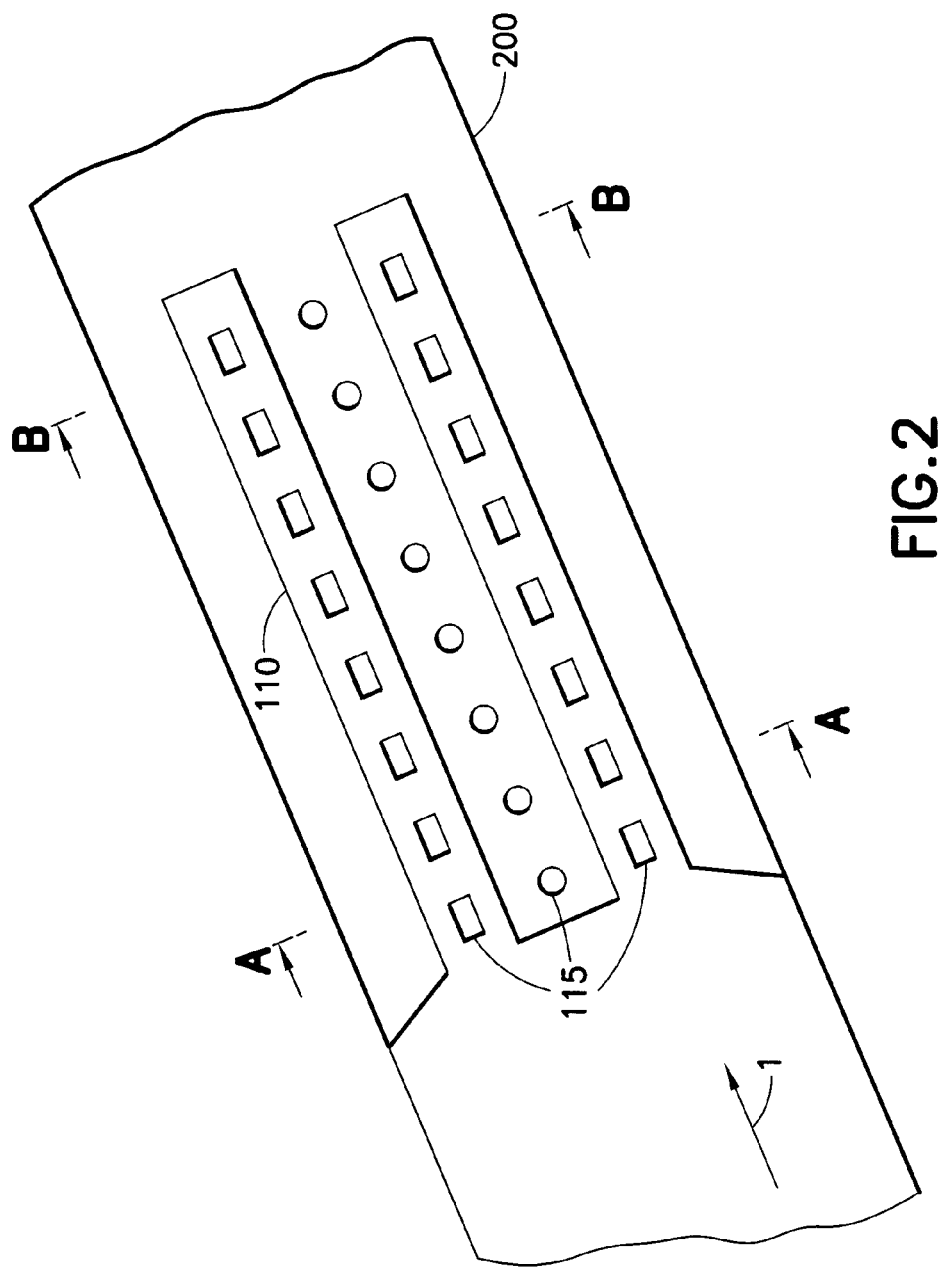
FIG. 2 illustrates a top view of a device with a low thermal mass suspended within a channel, according to some embodiments.

FIG. 2 shows a top view of the device 100 with a low thermal mass suspended within the channel 200. Sensing layers 160 (see FIG. 3) are configured on the microstructure or substrate 110 and attached to the channel 200. The microstructure 110 maybe integrally attached to the channel 200 or possibly attached via sensing layer patch (not shown). The sensing layers 160 (see FIG. 3) can be configured on the microstructure 110 to adsorb molecules of a selected component, such as, mercury or hydrogen sulfide vapor, from hydrocarbon fluids and/or natural gas 1 (designated by an arrow showing the direction of the flow) passing over it. FIG. 2 shows etching holes 115 positioned within the microstructure 110. The microstructure 110 as described above provides an advantage of having a low thermal mass and positioned in the flow 1 of the channel 200, thus preventing any stagnant layers on the surface. The low thermal mass allows for a rapid increase in temperature to re-evaporate the mercury and also allows for low power consumption if the device is operated at elevated temperatures, as further discussed below.

According to some embodiments, it is noted that there can be one or more identical devices positioned approximate the device 100 within the channel 200. Wherein at least one device of the one or more device can be created in a closed environment within the channel that acts as one of a reference feature or additional sensing features or both. It is also possible the microstructure 110 may include: one or more regions of sensing levels; one or more regions of a reference feature; one or more regions that sense different components; one or more regions that sense different levels of one or more components; or some combination thereof.

Figure 3:
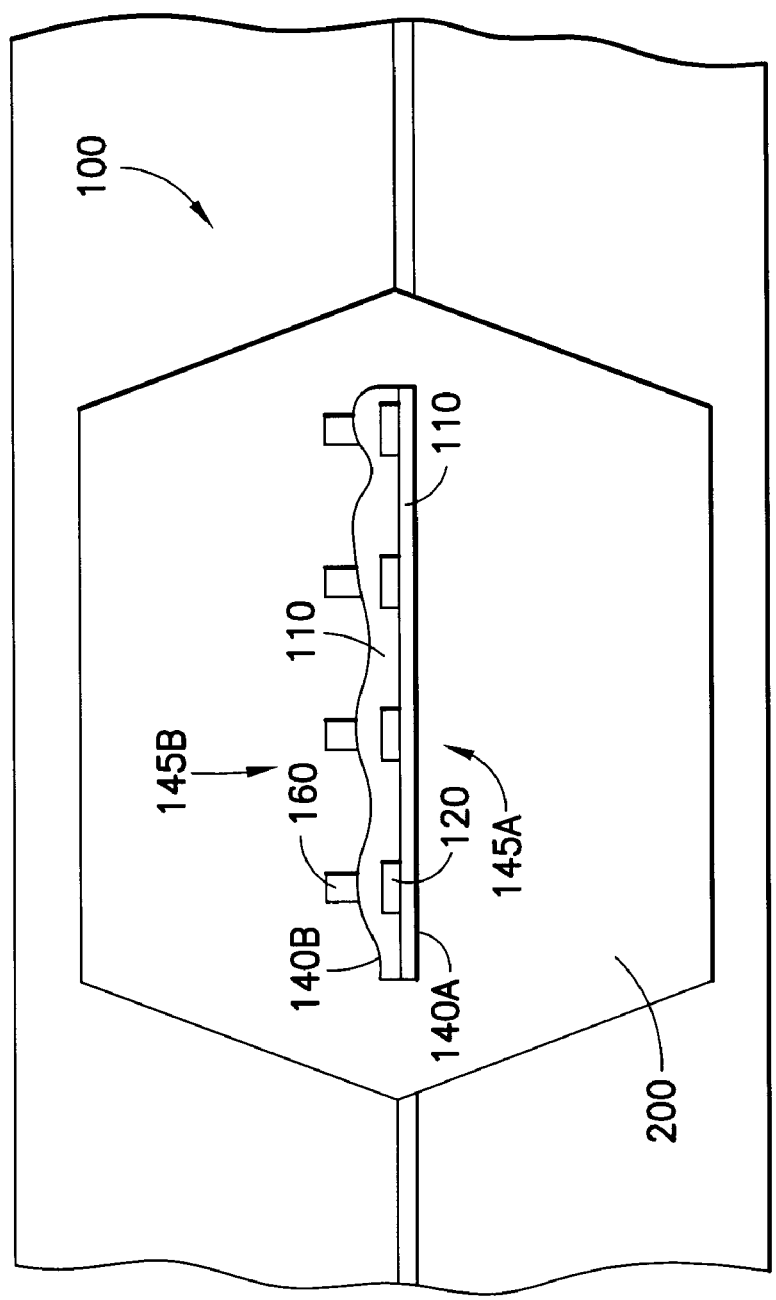
FIG. 3 illustrates a cross-sectional "A" view of FIG. 2 without the etching holes view of the device that is suspended within the channel, according to some embodiments.
Figure 4:
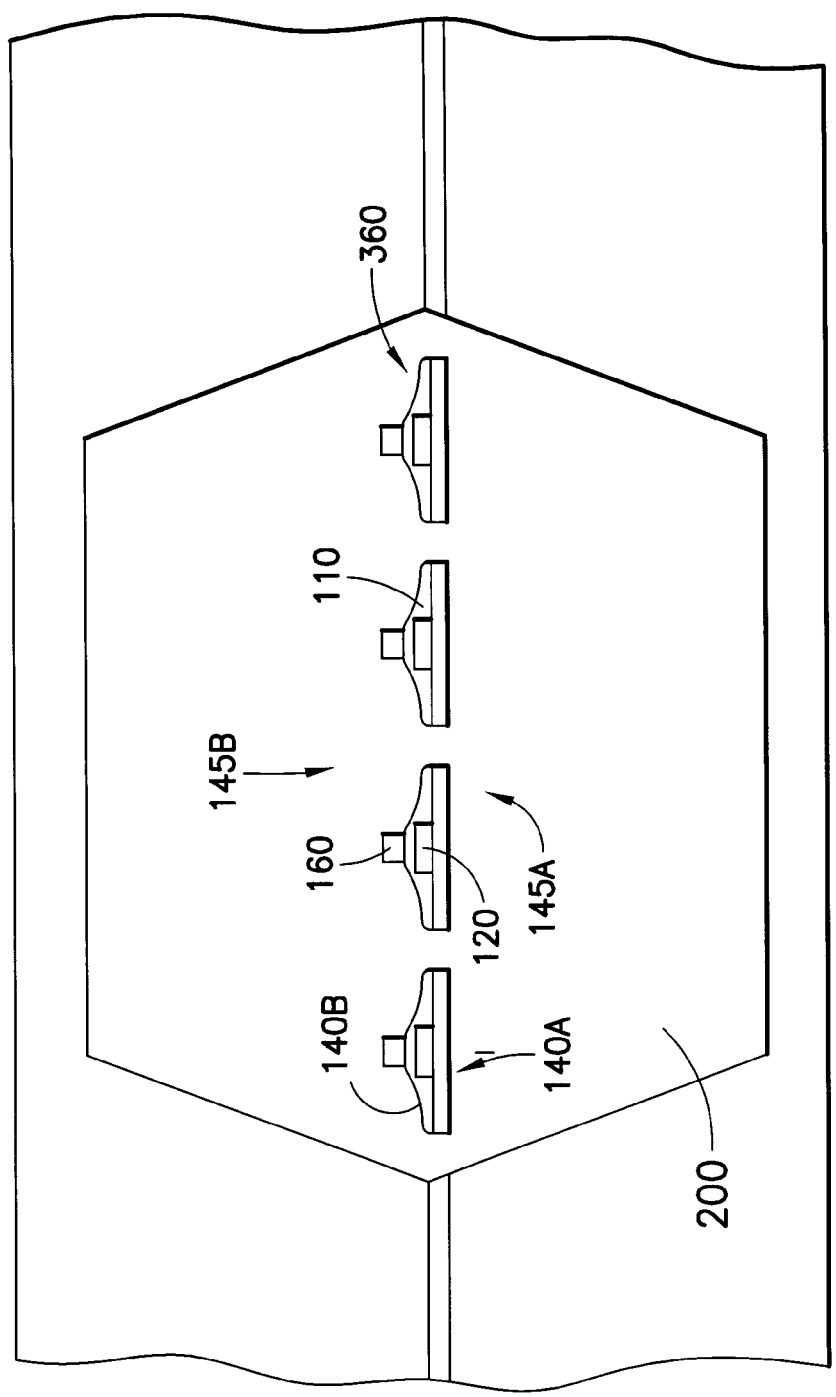
FIG. 4 illustrates a cross-sectional "B" view of FIG. 2 with the etching holes view of the device that is suspended within the channel, according to some embodiments.

Referring to FIGS. 3 and 4, FIG. 3 shows a cross-sectional "A" view of FIG. 2, with the microstructure 110 suspended within the channel 200. The microstructure 110 includes a supporting layer 140A and an insulating layer 140B. Controllable heater elements 120 are disposed on the supporting layer 140A to form a heating side 145A of microstructure 110. A sensing layer 160 is located on insulating layer 140B of the microstructure 110 to form sensor side 145B. The channel 200 or flow like device includes an inlet (not shown) and an outlet (not shown) for the flow of hydrocarbon fluids and/or natural gas 1 (see arrow in FIG. 1). Hydrocarbon fluids and/or natural gas is represented by arrows 1 (see arrow in FIG. 1), enters through the inlet (not shown), flows around the microstructure 110, and exits via the outlet (not shown). Sensing layer 160 is configured to adsorb molecules of a selected component, such as, mercury or hydrogen sulfide vapor, from hydrocarbon fluids and/or natural gas passing over sensing side 145B of the microstructure 110. Discussed below is an aspect of an embodiment of the microstructure which has at least two regions, a first region is used for sensing and a second region can be used for as a reference feature. For example, FIG. 4 shows it is possible a reference element 360 can be configured to adsorb molecules of the selected component at a substantially lower rate than sensing layer 160 and be located approximate the sensing layer 160 on the sensing side 145B of the microstructure 110. Such that, the reference element 360 can be configured to adsorb molecules of the selected component at a substantially lower rate than sensing layer 160 (see FIG. 4). It is also noted that more than one sensing layer and/or reference element may be located on the insulating layer 140B to form sensor side 145B of the microstructure 110. Further, it is noted that other regions on the insulating layer 140B that forms the sensor side 145B of the microstructure 110 can include regions for sensing one or more components at one or more sensing levels.

Still referring to FIG. 3, the controllable heater elements 120 can provide several advantages to the operation of the device 100, among others things, the controllable heater elements 120 along with the low thermal mass of the microstructure 110 allows for rapid increase in temperature to re-evaporate the mercury while at a lower power consumption if the device is operated at elevated temperatures. The notable feature is the controllability of the heater element 120 which provides controlled heat to the microstructure for a controlled or specific time which can translate into lower power consumption. This lower power consumption of the controllable heater elements 120 can be a significant advantage due to providing operational capabilities in oil and gas field applications including wellsite and subterranean environments where uses of high power consumption devices are not feasible. So, the controllable heat feature in combination with the low thermal resistance design of the microstructure 110 provides unique advantages. For example, thermal resistance is the temperature difference across a structure when a unit of heat energy flows through it in unit time. This means it is a measured temperature of how hard (or how much time) it takes for heat to conduct along a structure or material. Thus, heat conducts easily through a material when there is a low thermal resistance, and when the heat does not conduct easily through the material it has a high thermal resistance. So, because the microstructure 110 is suspended within the channel 200 and does not have other material that would require more thermal resistance, e.g., heating up other material on the microstructure or a casing around the microstructure, heat from the controllable heater element 120 (on the supporting layer 140A) readily conducts through the microstructure 110 to the insulating layer 140B to heat the sensing layer 160 during the re-evaporation process. Because the controllable heater element 120 is controllable and that the microstructure 110 has a low thermal mass it takes less heat and less time to complete the re-evaporation process. This is a unique advantage over similar known devices. It is possible by having the controllable heater capabilities that this feature reduces the effects of electromigration due to the microstructure 110 being exposed to less excessive high temperatures over that which is required to re-evaporate the mercury, e.g., regeneration temperature. As noted above, the low thermal mass along with the controllable heat feature provides for a quicker re-evaluation or regeneration process that allows for more operational time for the detection of the specified components such as mercury or hydrogen sulfide vapour while in the oil and gas field applications including wellsite and subterranean environments at one or more depths or locations. It is noted that operational time downhole or in an oil and gas field applications including wellsite and subterranean environments is very costly and any technology that can reduce the expense will be a significant technological advantage within the oil and gas industry along with other industries.

Still referring to FIGS. 3 and 4, the controllable heater elements 120 can include an adhesion layer (not shown) that is deposited on supporting layer 140A of the microstructure 110. The adhesion layer (not shown) provides the adhesion of controllable heater element 120 to supporting layer 140A of the microstructure 110. The adhesion layer (not shown) is deposited on supporting layer 140A using known evaporation techniques. In particular, adhesion layer (not shown) may be formed from materials that do not significantly affect the resistivity of controllable heater element 120. Further, when controllable heater element 120 is turned-on during a re-evaporation process, the controllable heater element 120 provides heat substantially evenly over supporting layer 140A of the microstructure 110.

Still referring to FIGS. 3 and 4, FIG. 3 shows a cross-sectional "A" view of FIG. 2 without the etching holes in the microstructure 110. FIG. 4 shows a cross-sectional "B" view of FIG. 2 with the etching holes in the microstructure or substrate 110, wherein the microstructure 110 suspended within the channel 200 has a supporting layer 140A. The microstructure 110 may be formed from titanium nitride (TiN) which is a material that has properties and characteristics suitable for use in high temperatures and in oil and gas field applications including wellsite and subterranean environments. Further, titanium nitride is an extremely hard ceramic material that has a non-toxic exterior and can be joined to other metals by film technologies and is also very conductive. It is possible other materials maybe used for the microstructure such as alumina ceramic.

Still referring to FIGS. 3-4, as noted above, the sensing layer 160 is located on insulating layer 140B to form sensor side 145B of microstructure or substrate. The sensing layer 160 can be arranged on the insulating layer 140B by one or more designs such as a geometrical layout, non-uniform layout, uniform layout or any combination thereof. In particular, the sensing layer 160 can include a single metal trace that is deposited on the insulating layer 140B of microstructure 110. Metal trace (not shown) has a chemical characteristic for the selected component to be detected. For example, metal trace (not shown) may be gold (Au). Gold is desirable for the detection of mercury and hydrogen sulfide vapor because gold is capable of adsorbing molecules of such gases. Known adhesion processing techniques may be used such as an adhesion layer to assist the adhesion of the metal trace to the insulating layer 140B of the microstructure 110.

Figure 5:
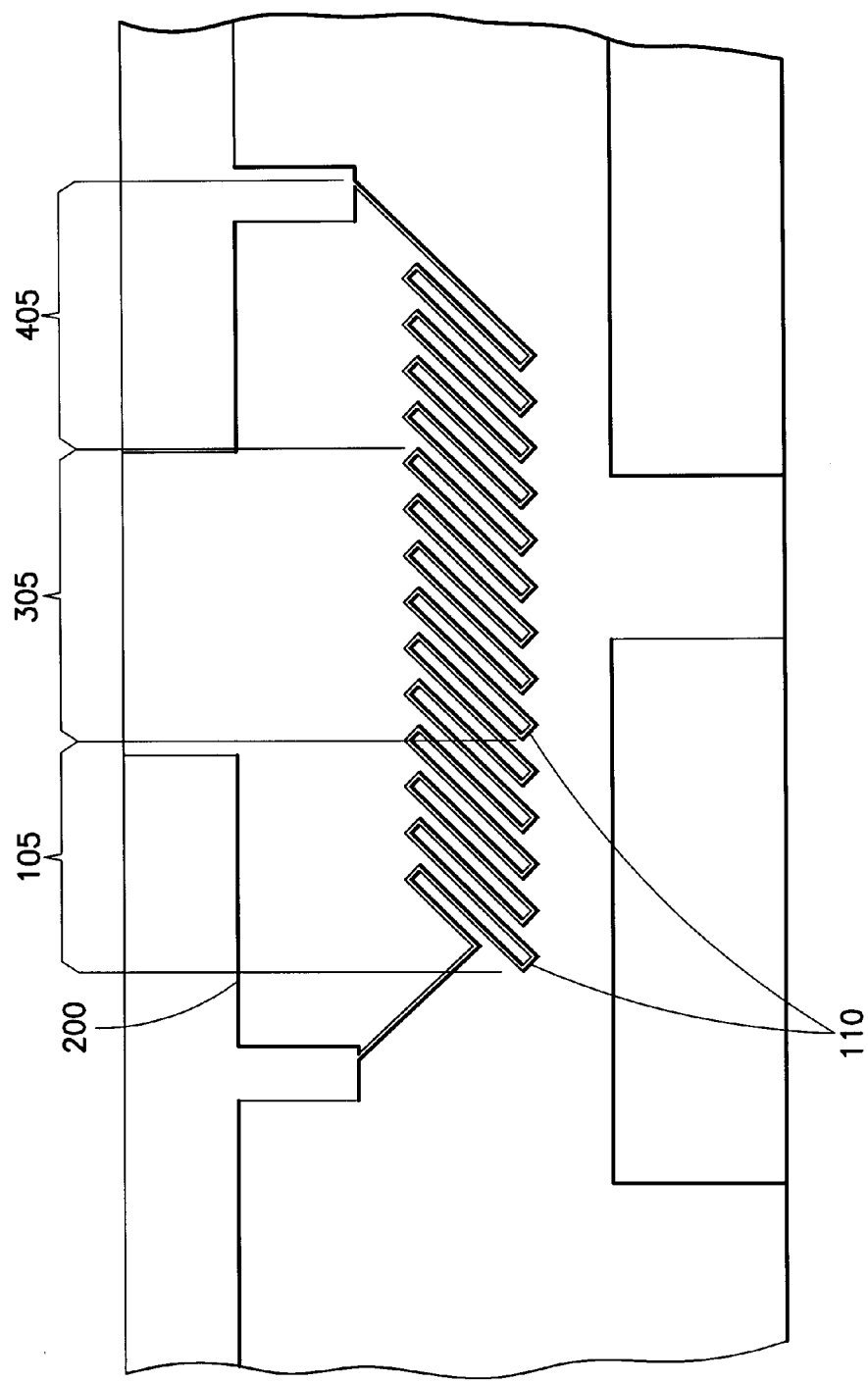
FIG. 5 illustrates a suspended microstructure that consists of at least three regions, the first region covered with gold, a second region covered with a non-amalgam forming metal or an insensitive layer and a third region that is a second sensitive layer, according to some embodiments.

Referring to FIG. 5, according to some embodiments, there are many materials other than mercury that form an amalgam. An amalgam is a substance formed by the reaction of some other substance with mercury, for example hydrocarbon fluids and natural gas. Some of the other materials that form an amalgam include silver, copper, palladium chloride and many alloys. Each of these layers can have a different response on the absorption of mercury and/or other components. The combination of sensors with different sensing layers can open up many possibilities to distinguish between mercury and other components. For example, at least one method to increase sensitivity is the use of porous gold often called black gold. It is noted that some metals cannot form amalgams with mercury, notably iron and platinum. However, platinum may be used in combination with gold and used as a reference.

Still referring to FIG. 5, FIG. 5 shows a suspended microstructure 110 that consists of at least three regions, the first region 105 covered with gold, a second region 305 covered with a non-amalgam forming metal or an insensitive layer and a third region 405 that is a second sensitive layer. Wherein all three regions are located on the insulating layer (not shown) of the sensor side (not shown) of microstructure or substrate 110. By providing electrical leads directly and separately to the first 105, second 305 and third 405 regions, it is possible to very accurately measure and control the resistance of each region. By putting the three regions together on the same microstructure 110 and suspended in the channel 200, this arrangement or design provides for the additional advantage of controlling the suspended temperature precisely thru the non-amalgam region (second region 305), where the resistance does not change with mercury concentration, while detecting mercury concentration with the gold region (first region 105) and detecting concentrations at one or more different sensitivity levels or even at the same level for the third region.

Still referring to FIG. 5, a combination of an insensitive layer (second region 305) with two different sensitive layers (first region 105 and third region 405) will have the advantages of both methods. The insensitive layer (second region 305) can be used as a reference whereas the two sensitive layers (first region 105 and third region 405) can have a different response on the adsorption of mercury and/or other components. The two sensitive layers (first region 105 and third region 405) should be chosen in such a way that it will allow distinguishing between mercury and other components. As noted above, FIG. 5 can be seen as a three region suspended microstructure having a first region 105 with a gold layer, a second region 305 having an insensitive layer and a third region 405 that is a second sensitive layer.

Still referring to FIG. 5, according to another embodiment, the regenerating temperature of the thin film gold layers can depend on the component that is absorbed. For example, it is known that mercury molecules begin to release temperature at approximately 170 degrees Celsius (this temperature is disputed within this science community), whereas hydrogen sulfide molecules begin releasing at a temperature of approximately 260 degrees Celsius. Thus, this temperatures difference can be used to distinguish between mercury and hydrogen sulfide although it is unclear at which temperatures thiols and water are released. According to some embodiments, one method to use this effect may be by making a temperature scan after a measurement has been made. The temperature at which the resistance starts to decrease faster determines which components are released and this knowledge can be used to determine the mercury and/or hydrogen sulfide concentration. A combination of two sensitive layers is also useful in this approach since the release of the absorbed molecule is dependent on the material of the sensing layer.

Still referring to FIG. 5, according to another embodiment, this method uses the difference in absorption strength between different target components. For example, two gold resistors are kept at different temperatures in the gas stream. The difference in absorption and thus increase of resistance can be used to identify and determine the concentration of the analyte. The difference in absorption rate will be taken into account in the measurement.

Figure 6:
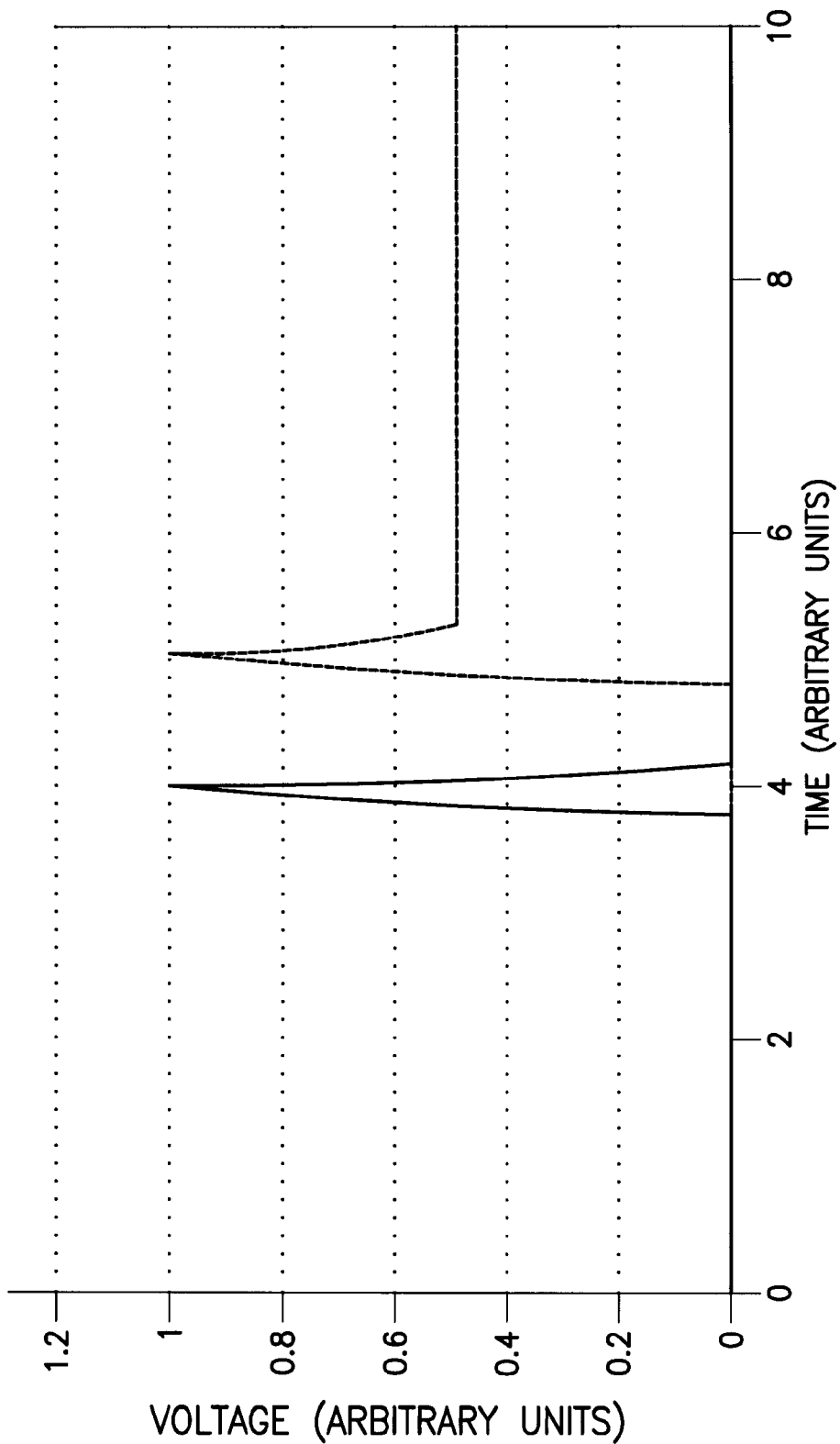
FIG. 6 illustrates a table showing arbitrary units between time and voltage that is a simulated response of a sensing layer (SL) with a sulfur insensitive heating material and a sulfur sensitive heating material, according to some embodiments.

FIG. 6 illustrates a table showing arbitrary units between time and voltage that is a simulated response of a sensing layer (SL) with a sulfur insensitive heating material and a sulfur sensitive heating material. It is noted that the high releasing temperature of hydrogen sulfide and most likely other sulfides can be used in peak identification for gas chromatography. In this method, a micro SL is used to detect peaks and determine the gas content in solution. This detector uses a heating element that is kept at a constant temperature and can operate in constant current or constant voltage modes. However, variations, in the electrical resistance due to the absorption or a chemical reaction are not tolerated. Therefore, an inert material is chosen as the electrical resistor. A resistor made of gold and operated below 260 degrees Celsius would allow for the identification of sulfur containing components. The gold resistor will not come back to its original value after a sulfur containing component has passed but will act as a "normal" SL on the passage of other components. The SL can be regenerated by a short heating cycle over 260 degrees Celsius. As a second SL, the gold SL can be placed in series with the inert SL.

Figure 7:
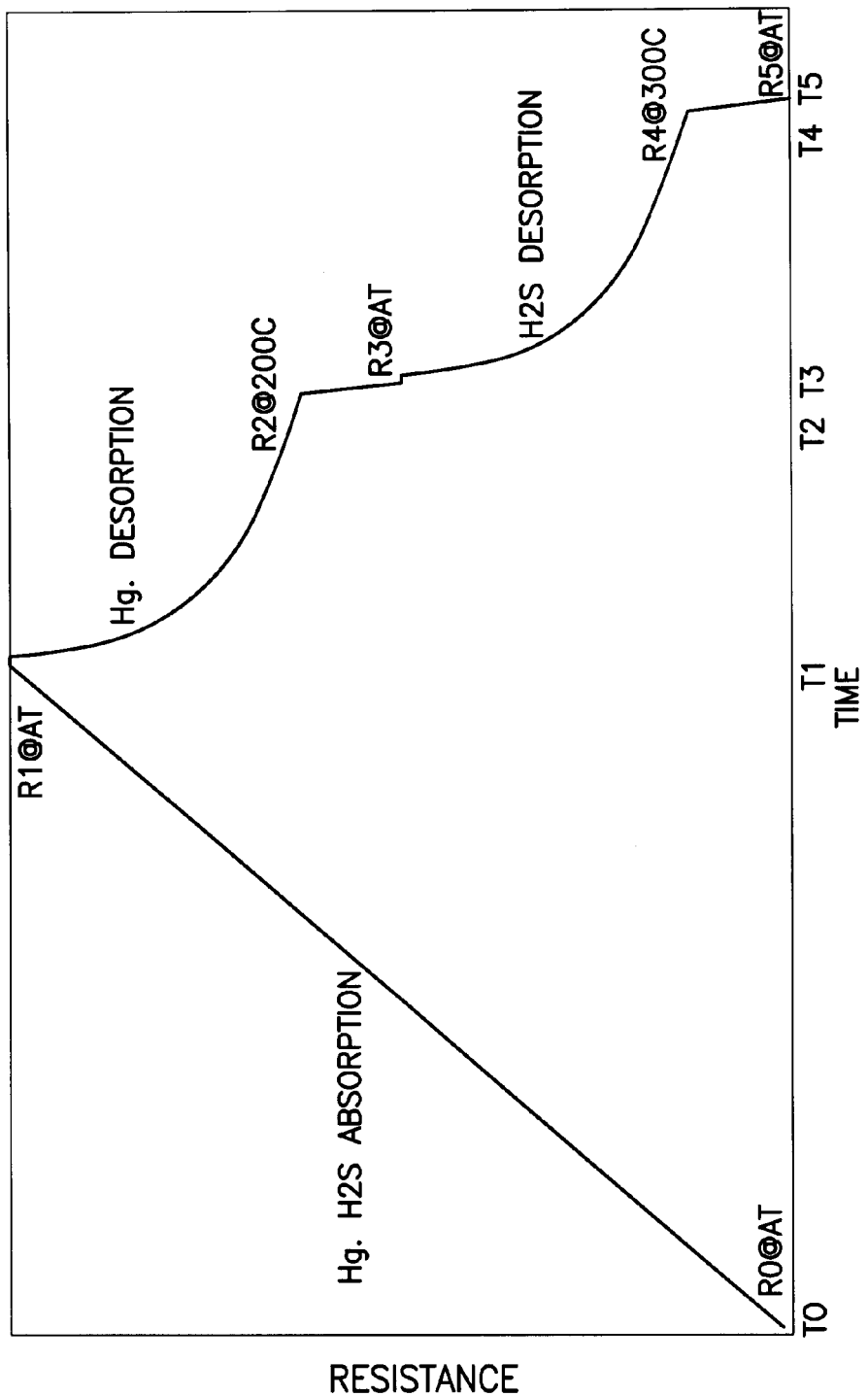
FIG. 7 illustrates a table showing units between resistance and time that is a simulated response of selective desorption based on time-controlled temperature manipulation of the low thermal mass microstructure, according to some embodiments.

FIG. 7 illustrates a table showing units between resistance and time that is a simulated response of selective desorption that takes advantage of the extremely low thermal mass of the sensing layer and the microstructure supporting layer, in combination with the temperature dependent desorption mechanism of mercury and/or H2S from a thin film gold (or other metal) resistance, according to at least one method. In particular, these features combined allow for the manipulation of the temperature of the device in a time-controlled manner, which leads to the manipulation of the absorption/desorption of the analytes. At least one example of the method is described as follows.

Still referring to FIG. 7, throughout the operation, flow of the analytes (which contains both Hg and H2S) is assumed to be constant. As shown in the following figure, during the time period T0 to T1, the device is kept at ambient temperature (AT). Both H2S and Hg are absorbed onto the gold resistance, which increases as the absorption goes on, before saturation. The resistance change rate from R0 to R1 (both at AT) is a measurement of $[H_2S]*S_{(H2S)}+[H_g]*S_{(Hg)}$, where $[H_g]$ is the concentration of mercury and $S_{(Hg)}$ is the sensitivity to mercury. Note that both axes are not to scale.

Still referring to FIG. 7, from T1 to T2, the sensor or sensing layer is heated, at a controlled rate up to 200 C. During this time period, most of the Hg previously absorbed on the gold surface will be released, causing a resistance decay, besides the resistance increase due to the temperature (which can be removed either by using a reference resistance, or by post-data-analysis. This resistance increase is not shown in the figure). T2-T1 is much smaller than T1-T0, so that the H2S absorption during time period T1 to T2 is negligible. This is achievable since the heating power is much larger compared to the thermal mass of the suspended device. From time T2 to T3, the device is cooled down almost instantaneously (on the order of millisecond), again, thanks to the low thermal mass, to the ambient temperature. This is done quickly enough that the absorption of H2S and Hg is negligible during this time period. The resistance change from R1 to R3 (both at AT) is a measurement of the amount of Hg desorbed from the device.

Still referring to FIG. 7, from T3 to T4, the device is again heated now up to 300 C, where all the H2S are desorbed. From T4 to T5, the device is cooled down to AT quickly. The resistance change between R3 and R5 (which is equal to R1, assuming no hysteresis) is a measurement of the amount of H2S desorbed from the device.

Figure 8:
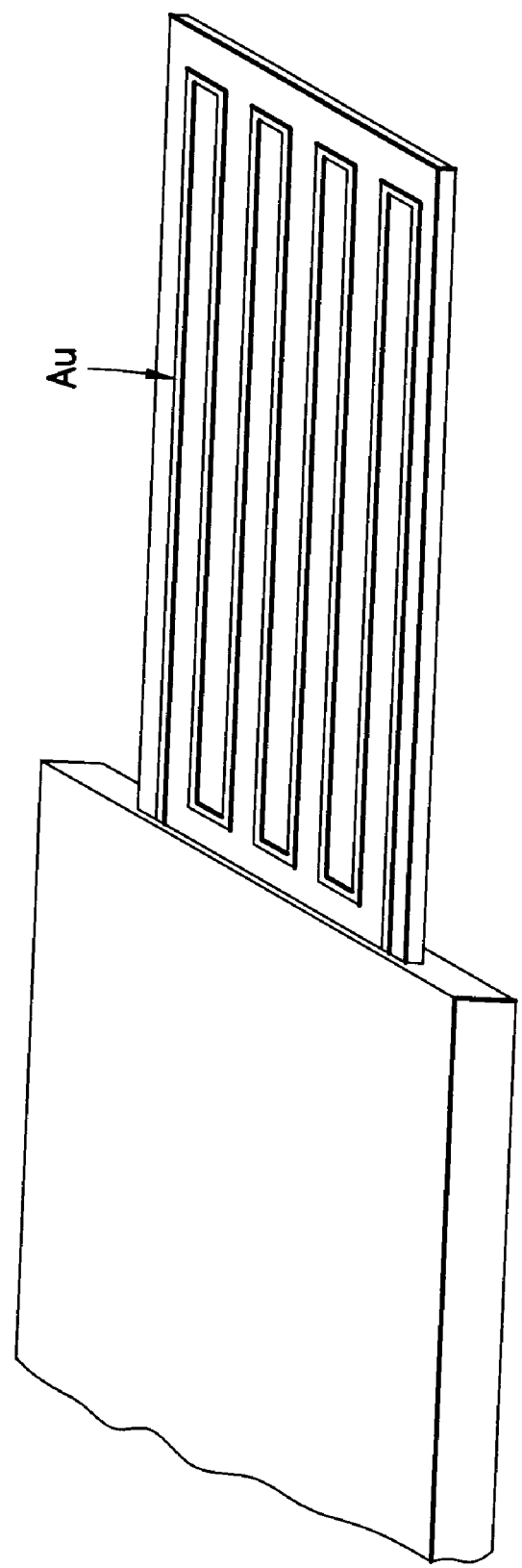
FIG. 8 illustrates a cantilever with gold resistor, the resonant frequency of the cantilever can be a measure for the mass whereas the gold resistor is used to measure the conductance, both can change due to the adsorption of mercury, according to some embodiments.

FIG. 8 illustrates a cantilever with gold resistor, the resonant frequency of the cantilever can be a measure for the mass whereas the gold resistor is used to measure the conductance, both can change due to the adsorption of mercury, according to some embodiments. This method uses the combination of a mass based sensor with a conductometric measurement that can be an alternative method to distinguish between mercury adsorption and the absorption of other components. The two different measurable parameters, i.e., mass and conductivity will vary as function of the mercury absorption (see FIG. 8). The absorption of an interfering gas, e.g., hydrogen sulfide, will not result in an identical response of both detectors compared to mercury. In other words, if hydrogen sulfide absorbs and causes a 20% increase in resistance, the measured weight will be different compared to the weight of mercury causing a 20% increase in resistance. Of course combinations with optical measurements are possible as well.

Figure 9A:
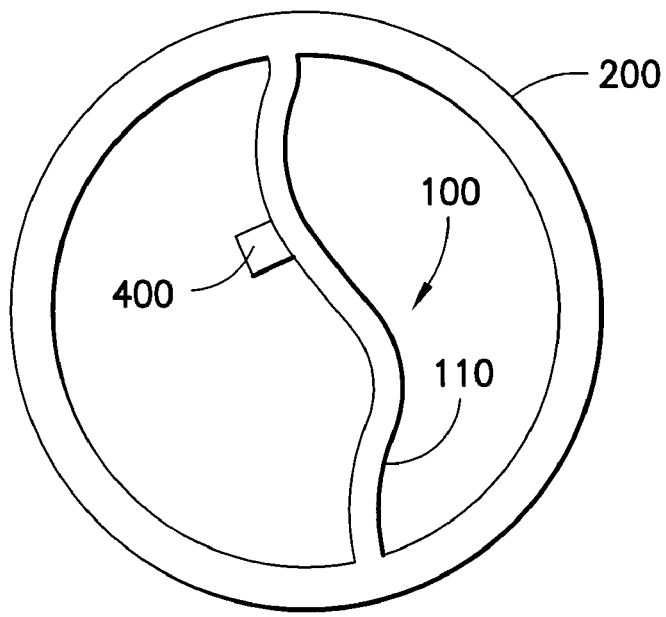
FIGS. 9A and 9B illustrate a side view of the microstructure suspended within the channel.
Figure 9B:
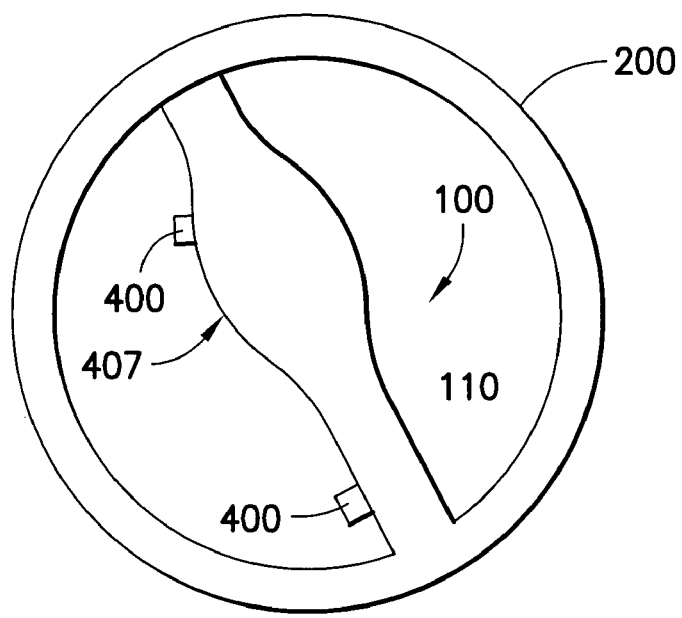

FIGS. 9A and 9B illustrate a side view of the conductometric sensor suspended within the channel, FIG. 9A shows a non-linear shape (e.g., wave-like) of the microstructure 110, so as to provide a disturbance in a flow of a fluid flowing through the channel, according to some embodiments. For example, it is possible the non-linear aspect may include a wavy like designed microstructure or added material to the microstructure to at least a portion of the microstructure. It is possible the microstructure could have one or more bumps such as a welded piece of material positioned on the microstructure 400. Further, FIG. 9B shows a microstructure that can be structured and arranged to have a variable thickness to provide a disturbance in a flow of a fluid flowing through the channel. For example, the variable thickness may include a bump such as a welded piece of material positioned on the microstructure 400 or the microstructure having a variable width 407.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Further, the disclosure has been described with reference to particular preferred embodiments, but variations within the spirit and scope of the disclosure will occur to those skilled in the art. It is noted that the foregoing examples have been provided merely for the purpose of explanation and are in no way to be construed as limiting of the present disclosure. While the present disclosure has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. A device for detecting gaseous mercury, the device comprising:
    a supporting substrate;
    at least one sensing layer disposed on the supporting substrate, wherein the at least one sensing layer absorbs molecules of gaseous mercury and at least one other gaseous chemical species;
    at least one controllable thermal device in communication with the at least one sensing layer, wherein the at least one controllable thermal device is configured to heat the at least one sensing layer to a release temperature of the gaseous mercury;
    at least one detecting and measuring resistance device in communication with the at least one sensing layer, wherein the at least one detecting and measuring resistance device is configured to produce resistance data that includes at least a first measure of resistance within the at least one sensing layer and a second measure of resistance within the at least one sensing layer; and
    a processor in communication with the at least one detecting and measuring resistance device and configured to receive the resistance data from the at least one detecting and measuring resistance device, wherein the processor is further configured to distinguish between the gaseous mercury and the at least one other gaseous chemical species based upon at least the first measure of resistance and the second measure of resistance within the at least one sensing layer.

2. The device according to claim 1,
    wherein the first measure of resistance is based upon resistance below the release temperature and the second measure of resistance is based upon resistance above the release temperature.

3. The device according to claim 1, wherein the at least one other gaseous chemical species is hydrogen sulfide.

4. The device according to claim 1, further comprising:
    an insulating layer disposed between the supporting substrate and the at least one sensing layer.

5. The device according to claim 1,
    wherein the at least one controllable thermal device is configured to heat the at least one sensing layer to a temperature sufficient to release the gaseous mercury and the at least one other chemical species from the at least one sensing layer.

6. The device according to claim 1, wherein the at least one controllable thermal device is configured to heat the at least one sensing layer to 400° C.

7. The device according to claim 1, wherein the at least one controllable thermal device is a conductive pathway disposed on at least a portion of the supporting substrate.

8. The device according to claim 1, wherein the at least one controllable thermal device applies heat to the at least one sensing layer when the electrical resistivity within the at least one sensing layer reaches a predetermined resistivity threshold.

9. The device according to claim 1, wherein the at least one sensing layer includes a first sensing layer and a second sensing layer.

10. The device according to claim 9, wherein the first sensing layer and the second sensing layer are formed from different materials and the first measure of resistance is based upon resistance within the first sensing layer and the second measure of resistance is based upon resistance within the second sensing layer.

11. The device according to claim 9, wherein (1) the at least one controllable thermal device is in communication with the first sensing layer and the second sensing layer, (2) the at least one controllable thermal device is configured to heat the first sensing layer to a first temperature and the second sensing layer to a second temperature, and (3) the first measure of resistance is based upon resistance within the first sensing layer at the first temperature and the second measure of resistance is based upon resistance within the second sensing layer at the second temperature.

12. The device according to claim 1, wherein the supporting substrate and the at least one sensing layer form a microstructure and the microstructure is suspended within a channel.

13. The device according to claim 12, wherein the microstructure includes a non-linear profile to provide a disturbance in a flow of a fluid through the channel.

14. The device according to claim 12, wherein the microstructure includes a variable thickness to provide a disturbance in a flow of a fluid flowing through the channel.

15. The device according to claim 1, further comprising:
    an insensitive reference element disposed on the supporting substrate;
    wherein the at least one detecting and measuring resistance device is in communication with the insensitive reference element and the at least one detecting and measuring resistance device is configured to produce resistance data that includes a reference measure of resistance within the insensitive reference element; and
    wherein the processor is configured to distinguish between the gaseous mercury and the at least one other gaseous chemical species based upon at least the first measure of resistance, the second measure of resistance, and the reference measure of resistance.

16. The device according to claim 15, wherein the insensitive reference element includes:
    a reference layer disposed on the supporting substrate; and
    a gas impermeable layer disposed on at least a portion of the reference layer to prevent absorption of at least one of the gaseous mercury or the at least one other gaseous chemical species.

17. The device according to claim 1, wherein the at least one sensing layer is a porous metal.

18. The device according to claim 17, wherein the at least one sensing layer is black gold.

* * * * *